(12) United States Patent
Baumgart-Schmitt

(10) Patent No.: US 6,272,378 B1
(45) Date of Patent: Aug. 7, 2001

(54) DEVICE AND METHOD FOR DETERMINING SLEEP PROFILES

(75) Inventor: Rudolf Baumgart-Schmitt, Schmalkalden (DE)

(73) Assignee: 2RCW GmbH, Berlin (DE)

( * ) Notice: Subject to any disclaimer, the term of this patent is extended or adjusted under 35 U.S.C. 154(b) by 0 days.

(21) Appl. No.: 09/308,514

(22) PCT Filed: May 20, 1999

(86) PCT No.: PCT/DE97/02685

§ 371 Date: May 20, 1999

§ 102(e) Date: May 20, 1999

(87) PCT Pub. No.: WO98/22019

PCT Pub. Date: May 28, 1998

(30) Foreign Application Priority Data

Nov. 21, 1996 (DE) .............................. 196 49 991

(51) Int. Cl.⁷ .................................................. A61B 05/04
(52) U.S. Cl. ................................................... 600/544
(58) Field of Search ........................... 600/300, 544, 600/545

(56) References Cited

U.S. PATENT DOCUMENTS

| | | | |
|---|---|---|---|
| 4,776,345 | * 10/1988 | Cohen et al. | 600/544 |
| 5,154,180 | 10/1992 | Blanchet et al. | |
| 5,299,118 | 3/1994 | Martens et al. | |
| 5,520,176 | * 5/1996 | Cohen | 600/300 |
| 5,999,846 | * 12/1999 | Pardey et al. | 600/544 |

FOREIGN PATENT DOCUMENTS

| | | |
|---|---|---|
| 0438945 | 7/1991 | (EP) . |
| 0773504 | 5/1997 | (EP) . |

OTHER PUBLICATIONS

Pfurtscheller, G. et al, "Sleep Classification in Infants . . . ", Biomedizinische Technik, Jun. 1992, vol. 37, No. 6, pp. 122–130.

Gerhardt, D. et al, "Atemmuster und Schalfstadienerkennung . . . ", Technisches Messen, Mar. 1995, vol. 62, No. 3, pp. 113–116.

Belenky, G. et al, "Discrimination of Rested from Sleep-Deprived . . . ", International Conference on Neural Networks Council, 1994, vol. 6, pp. 3437–4179, in particular pp. 3521–3524.

* cited by examiner

*Primary Examiner*—Robert L. Nasser
(74) *Attorney, Agent, or Firm*—Collard & Roe, PC.

(57) ABSTRACT

The invention relates to a device and a method for determining sleep profiles. The aim of the invention is to develop a device and a method which automatically generate a sleep stage classification with a grading of approximately 85% (measured according to the crosscorrelation function between automatically and manually generated sleep profiles) with negligible discomfort to the sleeper caused by additional technical equipment in his or her ordinary environment. The inventive device is characterized in that an electrode strip with a preamplifier (active electrode) working on the basis of a single frontal EEG channel is placed symmetrical to the nose root and is connected to a measuring and analysis unit controlled by a microprocessor and working autonomously. The method is characterized in that the EEG signal is compressed according to characteristics, stored and transmitted to a computer after this preprocessing, and classification according to sleep stages occurs in the computer by means of a population of neuronal networks.

17 Claims, 7 Drawing Sheets

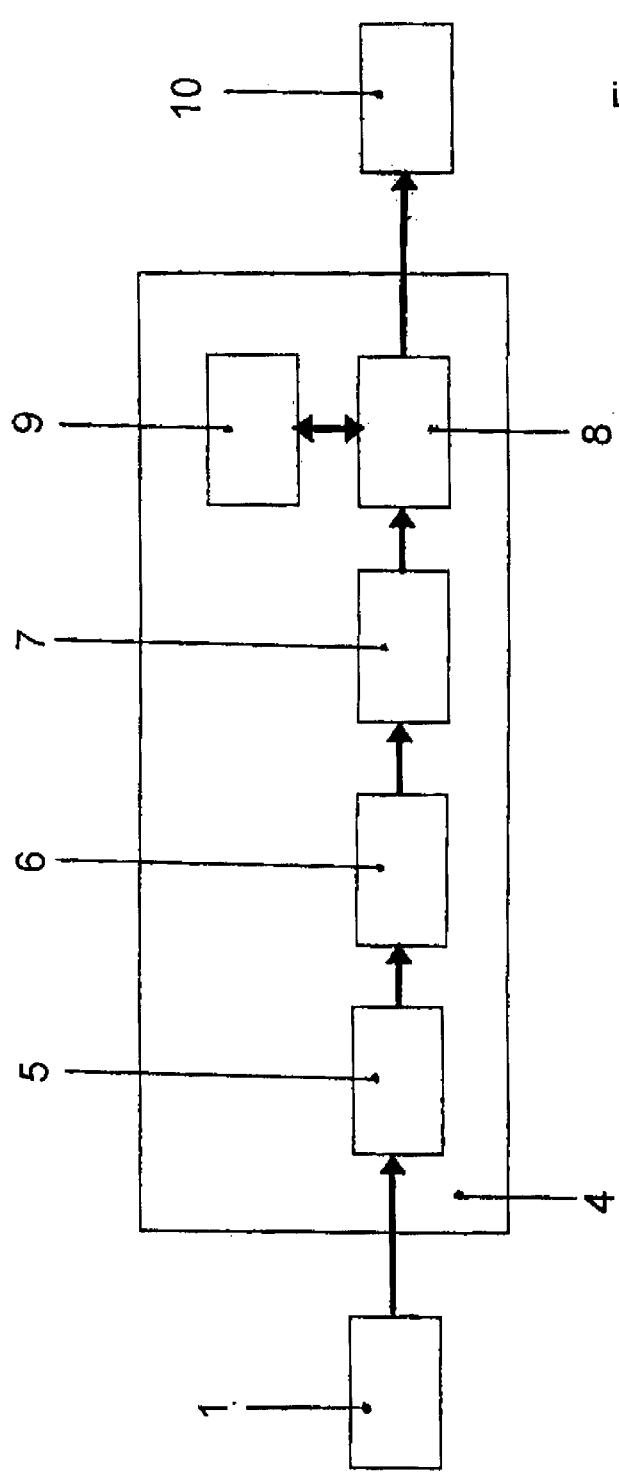
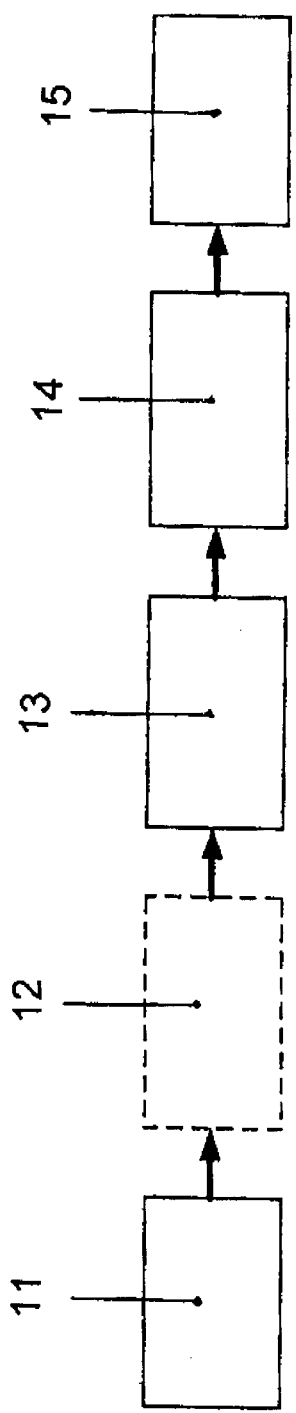
Figure 2
Figure 3

DEVICE AND METHOD FOR DETERMINING SLEEP PROFILES

The invention relates to a device and a method for the determination of sleep profiles.

In the current state of research and therapy, diagnosis of chronic and severe disturbances of sleep are secured by carrying out polygraphic tracings during the night by means of EEG-amplifiers, in laboratories which are specially equipped for this purpose. Trained and experienced personnel are required for operating such laboratories, including mainly polygraph assistants and sleep stage scorers. The latter carry out a visual sleep stage classification according to the rules of Rechtschaffen and Kales on the basis of at least one central EEC-lead, one EMG-lead and one EOC-lead.

Now, a sleep analyzer based on one single EEG-channel with a classic central lead position is introduced in U.S. Pat. No. 5,154,180. In connection with this method, the user himself has to preset by experimentation a threshold that substantially influences the number of resulting classifications and thus the number of resulting sleep stages.

A further significant drawback of this solution is that the method introduced in U.S. Pat. No. 5,154,180 corresponds with a cluster method, which by nature is not capable of realizing nonlinear associations of EEG-epochs with sleep stages because no sleep profile usable for diagnostic purposes can be generated solely from similar characteristics. Therefore, it is not possible on the basis of said solution proposed in U.S. Pat. No. 5,154,180 to generate a sleep profile that is comparable with a sleep profile developed by sleep experts.

Now, another method for the automatic classification of sleep stages is introduced in U.S. Pat. No. 5,299,118 that is not afflicted with said drawbacks. Every effort is made in connection with said method to offer all potentially available information and to create a system that satisfies the highest requirements. With respect to extraction of characteristics, said system contains everything that corresponds with the international state of system analysis of the year 1991. The method itself is based on 64 analog channels and operates with very high expenditure in terms of storage and computer capacities. The realization of said solution is consequently connected with relatively high costs and therefore preferably reserved for stationary application in sleep laboratories.

Furthermore, the employment of this system requires an acclimatization phase on part of the patient as well, who has to get used to both the changed environmental conditions of the sleep laboratory and the multitude of electrodes attached to the skull and face.

However, since sleep laboratories are available only in a very low number and tests in a sleep laboratory are, furthermore, very cost-intensive, it is necessary to make a tentative diagnosis before a patient is referred to a costly sleep laboratory.

In the current state of the art, no ambulatory equipment is available to the privately practicing physician for objectively evaluating the quality of sleep, and the physician is therefore dependent upon the subjective statements of his patients.

For example, the present state of tentative diagnosis consists in answering the questions of a questionnaire relating to subjective data on the medical history (sleep anamnesis) particularly concerning which type of sleep disorder is involved. In other cases, the tentative diagnosis is made with an ambulatory actometer. This instrument registers the movements of the arm and in this way supplies information about activity and rest phases during the sleep. Such methods, however, cannot supply any objective evaluation of the quality of sleep. Exact diagnosis and therapy derived therefrom, for example with medications require an objective evaluation. Patients currently much too often take sleep-inducing medications without having available to them an objective correlate with respect to their subjectively perceived complaints. Sleep profiles, as time series of sleep stages, supply this objective "copy" of the quality of sleep if interpreted in a suitable manner, and give clear indications of pathological processes.

Therefore, there is currently a worldwide demand for generating sleep profiles automatically with negligible discomfort to the sleeper caused by additional technical equipment in his or her ordinary environment in order to make available objective quality measures for the quality of sleep and to permit ambulatory diagnosis. Furthermore, the costs for ambulatory diagnoses are to be kept as low as possible. This can be accomplished especially when no trained medical technicians are needed for mounting the electrodes and for operating the equipment for data acquisition and data evaluation.

Furthermore, it has to be noted that in the state of the art, data on night sleep are exclusively collected by physiological methods, whereas data on the wake state are exclusively gathered with psychological parameters of behavior and the condition of being.

The falling-asleep behavior during the day and the performance became evaluable only with the very costly multiple sleep latency test (MSLT).

Therefore, the invention is based on the problem of developing a device and a method for the determination of sleep profiles, which automatically generate a sleep stage classification with a grading of about 85% (measured according to the crosscorrelation function between automatically and manually generated sleep profiles) with negligible discomfort to the sleeper caused by additional technical equipment in his or her normal environment, permitting in this way ambulatory diagnoses, whereby the newly development arrangement, furthermore, is characterized by minimal manufacturing expenditure as well as practical equipment technology with high operational safety and reliability that can be easily handled by each patient on his or her own, and which, moreover, is capable of registering even a 24-hour continuum in a physiologically objective manner by a simple method at favorable cost.

According to the invention, said problem is solved by an arrangement for the determination of sleep profiles. Said arrangement operates on the basis of one single frontal EEG-channel and consists of an electrode strip with a preamplifier (active electrode). Said electrode strip is placed on the forehead and is connected to an autonomously working measuring and analysis unit controlled by a microprocessor. Said unit, which is supplied with energy via a storage battery (accumulator), consists of analog filters, a final amplifier, an analog-to-digital converter, a microcontroller with internal system software, a memory, a display and an operating keyboard, and is connected for the further data analysis via a serial interface by means of a light conductor cable (potential separation) to a commercially available PC with special software for adaptive classification by means of populations of neural networks for visualizing the electric potentials of the brain as well as the sleep and awake profiles.

Said electric potentials of the brain are processed in real time by the measuring, storing and analysis unit controlled by the microprocessor. According to the invention, said device operates in two modes: the so-called off-line mode and the on-line mode. Said terms relate to the fact that it is possible to couple the unit with a computer, preferably with a laptop. Off-line mode means that the unit operates autonomously, whereby it detects the electric potentials of the brain, extracts and stores characteristics relevant to the classification, as well as classifies sleep stages, if need be in real time (provided they amount to 30 seconds), and stores such sleep stages as a function or time.

The highest stage of content-related data compression is reached through such generation of sleep profiles in real time. The off-line mode is the primary operating mode. Temporarily connecting the computer at the end of a night serves the purpose of generating the sleep profiles and their graphic display. The on-line mode requires continuous coupling with a separate unit for storing the original electric potentials of the brain. Such separate unit may be a commercially available computer or a storage and transmitting unit controlled by a microprocessor. In both operating modes, classification of the sleep stages is carried out by populations of neural networks. Their topological parameters were optimized through evolutionary and genetic algorithms on a parallel computer with the SASCIA system (Sleep Analysis System to Challenge Innovative Artificial neural networks).

It is characteristic for the component for tapping off the electric potentials of the brain that the electrodes are secured on a flexible electrode strip containing the pre-amplifier of the EEC-signal.

Because of its design as defined by the invention, said electrode strip with the integrated preamplifier can be easily secured on the forehead without any help from another person.

One of the supporting ideas of the invention substantially consists in that the method is limited to the evaluation of the potentials as they can be tapped off in the forehead position, using thereby only one information channel from the difference formation of both forehead potentials as they can be acquired on the electrodes disposed symmetrically relative to the nose.

This core idea of the invention basically contradicts the currently accepted instruction for electrode placement in view of the generation of sleep profiles.

The contradiction is obviously primarily substantiated in that the strongest electrical influences have to be expected in said lead position due to movements of the eyes.

However, it is precisely in spite of said influences which—are frequently referred to as eye movement artifacts that—it is possible by means of the solution as defined by the invention, with the electrode strip with preamplifier (active electrode) placed on the forehead, to carry out the required sleep stage classification as a precondition for the generation of sleep profiles.

Furthermore, however, the forehead position as defined by the invention also permits freedom of movement during sleeping to the greatest possible extent.

Therefore, because of the solution as defined by the invention it is possible to provide the physician with a device which, as compared to the devices of the state of the art, is not perceived as annoying by the patient.

It is important also, furthermore, that the active electrode arrangement employed for data acquisition is of a type that reduces interfering influences of electric systems and devices to a minimum.

Therefore, the decisive feature of the invention consists in that any separate acquisition of the muscle potentials and eye movements—which is actually required by the state of the art—is deliberately omitted, and that exclusively and only the information is used that can be extracted in the region of the forehead of the patient from the potential difference of electrodes arranged symmetrically relative to the nose.

Furthermore, it is a characteristic feature that the EEG-signal as an analog signal is already subjected to an amplification near its site where it is derived, and that the signal source is in this way mainly subjected to an impedance conversion.

A difference amplifier with three electrodes was used in order to keep interference stray pickup as low as possible. While one electrode, preferably the center electrode, produces the reference point, the difference of the two other electrodes is amplified by the circuit with factor 100. The high-pass filter ($f_g$=0.03 Hz) connected upstream of each of said two other electrodes eliminates the dc voltage component of the two signals, which is not important for the evaluations.

As mentioned before, the frontal position on the forehead was selected according to the invention for placing the ground and reference electrode as well as the preamplifier component and the electrodes for bipolar lead-off.

The forehead position above the nose as close as possible to the hairline serves as orientation for mounting the ground and reference electrode, whereby the electrodes for bipolar lead-off are mounted in a horizontal line to the right and left of the reference electrode with a fixed spacing from each other.

Said EEG-signals are then supplied to a battery-operated hand-held device, which is the measuring, storing and analysis device, where said signals are first filtered, subsequently amplified, then digitized for further processing, and thereafter either compressed according to characteristics and stored, or transmitted on-line to the PC.

The signal content of the EEG relevant to the sleep analysis amounts to about between 0.5 and 60 Hz. According to the invention, the DC potential component (0 Hz component) is not used for evaluating the sleep and generating a sleep profile.

The DC potential component may assume substantial values as compared to the frequency components here of interest and it is therefore suppressed already prior to the amplification.

The maximum signal voltage of the EEG $U_{ss}$ (without the dc potential component) is in the microvolt range and amounts to about 1 mV in the frontal lead positions. Particularly characteristic line curves with amplitudes that may amount to 1 $\mu$V are very significant for the further evaluation as defined by the invention.

Since the sleep analyzer is expected to be employed in the home environment, considerable network stray pick-up necessarily has to be expected. These technically conditioned artifacts are therefore eliminated.

In light of the characteristic properties of the EEC-signal and of the interferences, the following measures are implemented according to the invention in the analog part: Elimination of the 0-Hz component by high-pass filtration, filtering of the 50-Hz network stray pick-up, low-pass filtering of the signal with an upper limit frequency of 64 Hz in order to minimize as much as possible aliasing effects due to subsequent A/D conversion and equidistant scanning of 128 Hz, and to realize amplification with as little noise as possible, In addition to the active electrode described above, the analog part comprises the voltage supply as well as under-voltage switch-off substantially in the form of a filter bank (low-pass filter, 50 Hz filter, high-pass filter, and final amplifier).

According to the invention, the filter bank consists of a 50 Hz filter, a low-pass filter and a high-pass filter. Switched together, said filters supply a bandpass filter with $f_u=0.5$ Hz and $f_o=64$ Hz.

The 50-Hz filter is designed as a gyrator circuit and minimizes the network stray pick-up of the derived signal A usable signal is still supplied with a damping of over 30 dB and a bandwidth of 10 Hz even with higher hum voltages.

In accordance with the subsequently required digitalization of the signal, with 128 values per second according to the invention, the frequency range above the frequency (64 Hz) maximally representable according to Shannon's scanning theorem is almost completely suppressed for avoiding aliasing effects.

Since the power of the EEG-signal distinctly drops above 30 Hz, a low-pass filter of the 2nd order is employed for achieving the effects as defined by the invention. The limit frequency of said filter was fixed at 64 Hz.

To make the subsequent amplification possible it is necessary to remove the dc voltage component still inherent in the signal. For this purpose, provision is made for a high-pass filter according to the same circuit pattern as the low-pass filter. Its limit frequency of 0.3 Hz is adapted to the relevant frequency range of the EEG-signal.

The filter is followed downstream by a final amplifier which, according to the invention, amplifies the signal by factor 50. With the subsequent offset adjustment, the signal level according to the invention is in the range applicable for the A/D-converter.

Said amplified signal is now digitized and preprocessed for further computer processing and efficient storing.

According to the invention, the signals were scanned equidistantly at 128 values per second. The amplitude is coded according to the invention with 10 bits (maximum amplitude 1 mV, minimum resolution 1 $\mu$V →1000 digits= 10 bits resolution), and discretizing in 1024 stages is viewed as adequate.

Since about 7 mbyte (2 byte/value 128 values/s·60 s/min·60 min/h) data would be collected with uncompressed storage of the time signal of a complete night, expansion of the memory of the device to said size resulted in a high final price.

Furthermore, according to the invention, the signal is subjected to semantic compression because on-line generation of the sleep profiles is desired with the device as defined by the invention in Standalone operation, in connection with the consequently absolutely required minimization of the memory space requirements.

In this connection, the signal is subjected to extraction of characteristics. Classification-relevant characteristics were obtained within the framework of tests carried out as part of the preliminary work leading to the invention. Said characteristics are applied in the extraction of characteristics. The sum of the spectra over the 30 individual seconds of each epoch forms the base for computing the characteristic values of each epoch, whereby the power component of low-frequency ranges is reduced within the time range (formation of the first differences) by a high-pass filter. The spectra are then determined with a resolution of 1 Hz in the range of 1 to 63 Hz via rapid Fourier transformation.

The sleep profile comprises about 1000 30-second epochs.

According to the invention, only the classification-relevant EEG-characteristic "printouts" are stored for each of the periods. Comprehensive tests carried out within the framework of the work leading to the invention resulted in this connection in 15 to 20 relevant characteristic printouts.

This leads to a memory requirement of only about 50 kilobytes. An 8-bit microcontroller suffices for managing said memory and for performing the required preprocessing operations. Such controllers have a very good price/performance ratio and, furthermore, they can be employed in a very flexible way.

For example, an 80517A microcontroller was employed in the arrangement as defined by the invention. Said microcontroller is fully compatible downwardly to the 8051-family and, in terms of performance, ranks at the top end of the product line. This controller, which is cycled with 12 MHz, has an internal 10-bit A/D-converter. Of the 12 multiplexed analog channels available with this microcontroller, two are needed. One channel converts the EEG-signal and the second channel serves for monitoring the operating voltage. Now, if the operating voltage falls short of the permissible operating voltage of 4.5 volts, the controller changes to a waiting state and supplies a signal for the "resting condition" of the entire circuit. Only the display remains in the operational state and signalizes that the operating voltage fell short ("battery discharged").

The directly addressable memory areas of 64 kilobytes each for both the data and the commands are adequate for the application as defined by the invention. Owing to the variable clock pulse frequency of the controller (18 MHz is maximally possible) it is possible to even adjust for the existing requirements a reduced power consumption if higher clock pulse frequencies are waived. This so-called sleep mode is used in order to prolong the operating duration because of the limited capacity of the battery.

Controlling the LCD-displays, which supply information about the actual operating condition, poses no problems. The sleep data are stored in two sRAM's of 32 kilobytes each; their contents remain preserved by battery buffering even when the device as defined by the invention is switched off.

For recording the measured values, timer 2 of the controller was programmed according to the invention in such a way that an interrupt is triggered every 7.812 ms. The operating program if said interrupt carries out the A/D conversion and stores the measured value. If the device as defined by the invention is in the on-line mode, the interrupt operating program immediately issues the measured value to the serial interface.

It is also important for the invention that the data so obtained according to the invention arc serially transmitted from the interface to a PC via a glass fiber cable in order to assure potential separation from the mains. The transmission as such takes place unidirectionally with 9600 baud. An adapter (consisting of a photoelectric transistor and an amplifier) is required for said purpose on the PC side for readapting the signal.

The data received by the PC are visualized in the latter and stored on a fixed disk.

The method of determining sleep profiles is particularly characterized in that the electroencephalographically detected analog signal tapped off on a patient in the region of the forehead symmetrically relative to the root of the nose is filtered by means of the arrangement as defined by the invention, amplified, digitalized for further processing, and subsequently either compressed according to characteristics and stored, or after such preprocessing directly transmitted on-line to a computer, whereby the classification is carried out in the computer according to sleep stages by means of populations of neural networks which were topologically optimized by means of genetic and evolutionary algorithms, and whereby the body signals and the profiles are visualized and interactive processing is possible at the same time.

According to the invention, the following 14 characteristics are obtained and supplied to a classifier following digitalization and Fourier transformation of the analogously amplified and filtered EEC-signal:

Accumulated power density in the range of 1 to 4 Hz based on the overall power density (characteristic m1);

Accumulated power density in the range of 5 to 7 Hz based on the overall power density (characteristic m2);

Accumulated power density in the range of 8 to 11 Hz based on the overall power density (characteristic m3);

Accumulated power density in the range of 12 to 14 Hz based on the overall power density (characteristic m4);

Accumulated power density in the range of 15 to 30 Hz based on the overall power density (characteristic m5);

Accumulated power density in the range of 31 to 63 Hz based on the overall power density (characteristic m6);

Frequency at 25% of the overall power density (characteristic m7);

Frequency at 50% of the overall power density (characteristic m8);

Frequency at 75% of the overall power density (characteristic m9);

Frequency of the maximal power density value in the range of 1 to 4 Hz (characteristic m10);

Frequency of the maximal power density value in the range of 8 to 14 Hz (characteristic m11);

Frequency of the maximal power density value in the range of 21 to 30 Hz (characteristic m12);

Accumulated power density in the range of 50 to 60 Hz based on the overall power density (characteristic m13); and Number of the epoch based on the total number of epochs (characteristic m14).

While in the off-line mode, extraction of the characteristic takes place through the unit as defined by the invention, the extraction of the characteristic is handled in the on-line mode by the laptop. Use is made in this connection of identical algorithms as they are carried out also by the controller of the unit as defined by the invention.

The computed characteristic values are standardized in their totality in order to create a suitable base for further processing. Standardization is to be seen in close connection with the parameters of the neural networks employed for the classification. Overcontrolling or at least one unfavorable control of the units has to be expected if the standardization is coordinated inadequately. This can considerably deteriorate the classification by the instructed neuronal networks. Extreme variations of the individual characteristics and especially of the relative power densities are possible due to the interindividual variances of the EEG-characteristic printouts.

Standardization as defined by the invention is expected to effect in this case the generalization capabilities of the networks. Accordingly, each characteristic printout is reproduced over all epochs to a value range of between −2.0 and +2.0 and offered to the network as input data. It was necessary in this connection to make use of an image formation specification that reacts insensitively to "runaways".

So that a sleep stage can be allocated to each epoch with the help of said "printouts" of characteristics, a classifier is needed which is capable of learning and at the same time robust, and which, furthermore, is capable of resolving the nonlinear classification problem in the sleep stage analysis in spite of considerable interindividual deviations. According to the invention, populations of neuronal networks are employed for this purpose which were instructed with the error-back propagation (EBP) algorithm, and whose topological parameters were optimized by means of genetic and evolutionary algorithms.

It is important to the invention that the networks must resolve 7-class problems because a distinction is made between 4 sleep stages (sleep stages 1 to 4), the REM stage, the AWAKE stage and the MOVEMENT stage.

The networks are instructed on a parallel computer with the data of one or several manually classified nights. In the EBP-process, the weights of the individual units are improved by applying the characteristics (input pattern) to the inputs and comparison of the produced output values with the desired output values (instructional statements), with the objective that the deviations of the actual output values from the desired outputs for the input pattern are heading for a minimum via all patterns, on the average.

With said method as defined by the invention the networks arc capable of adapting their weights to the sets of learning data. Adaptation of the networks to a set of learning data, however, only remains the means for achieving a generalization efficiency as good as possible. The generalization efficiency can be estimated only via a set of test data which is not employed for adapting the weight.

This is to say that according to the invention, those weights of the networks are used in connection with which a minimum of the generalization error was achieved based on the number of learning steps carried out. Moreover, it is important to the invention that a great number of populations of networks were included in the instruction.

The topology of the networks and the learning parameters were optimized by simulated evolution in view of the characteristic vector selected by genetic algorithms. The SASCIA system (sleep analysis system to challenge artificial neural networks) was used for this purpose.

Furthermore, it is important to the invention that instructed networks perform the stage allocations to each epoch.

Important to the invention is in this connection the simultaneous use of three populations of n=8 networks each, whereby one network was instructed in each case with the data of one night. Various methods were compared as part of the preliminary work leading to the invention in order to find the most suitable cooperation of the networks in a population and of the populations among each other in the sense of a decision of the class allocation.

According to the invention, the classification is carried out according to the following methods:

The classification is first carried out separately with each network population, whereby the network populations differ from each other in that they were instructed based on 12 (characteristics m1 to m12), 13 (characteristics m1 to m13) and 14 characteristics. Thus the networks of population 1 have 12, the networks of population 2 have 13 and the networks of population 3 have 14 input units. The number of output units remains fixed at 7 for all networks in accordance with the number of classes. The number of hidden units in the two covered intermediate layers of the networks configured in a forwardly coupled hierarchical form varies according to the best reclassification performances found. Two steps are carried out population-specifically:

(1) For each epoch, the output unit with the maximal excitation is determined for each network, so that n=8 network-specific decisions are obtained.

(2) The median over all network-specific decisions supplies the class in which the respective epoch is to be classified. The formation of the median requires imaging of sleep stages in 7 natural numbers.

Once the decisions have been made for each population, the latter are combined in the sense of median formation. The synergy effects of three populations of neural networks and a total of 24 networks produce a robust classifier which can well handle or manage the high interindividual variation of the electric potentials of the brain, including sick test persons.

The sleep profiles generated on the basis of said classifier as defined by the invention have additional transitions between the sleep stages as compared to the expert profiles. Said transitions can be readily substantiated when viewing individual epochs separately.

Sleep experts, in addition to their knowledge with respect to the individual EEG-patterns, also employ knowledge relating to time horizons in the minute and hour ranges. This means that the allocation of sleep stages to individual epochs is influenced also by contexts in which the epochs are embedded. This relatedness to context cannot be managed by neural networks if the individual epochs are offered to the network for instruction in a random sequence. Context rules as defined by the invention must take this place and must help to enhance the sleep profiles via smoothing algorithms.

Therefore, starting from the differences between a sleep profile which was automatically generated by the neural network as defined by the invention, and the experts' profiles, which differences have to be minimized, the following rules are applied according to the invention in the method as defined by the invention:

The torn sleep stage REM-epochs of the profiles are converted into a monolithic block.

If the duration of the epochs embedded in the REM sleep stage is shorter than or equal to 40 seconds, said epochs are allocated to the REM sleep stage.

REM sleep stage occurring during the falling-asleep phase is allocated to sleep stage 1.

If the classifier proposes sleep stage REM over a time interval of maximally 80 seconds, said interval is allocated to sleep stage 1 as well.

Allocations to sleep stage 1 are converted into sleep stage 2 allocations if the duration of sleep stage 1 does not exceed one minute and the interval is embedded in sleep stages 2, 3 or 4.

If epochs of sleep stage 1 do not last longer than two minutes and are embedded between sleep stages 2 and REM, they are allocated to sleep stage 2.

Therefore, the following rules are important for the invention:

Rule 1: The torn REM-epochs of the profiles are picked out and converted into a monolithic block according to the following instruction:

rem, [rem], . . . ←rem, [stage 1], . . . with ←as "leads to" operator, and [ ] . . . as repeat operator. Break-off of the repeat takes place by network funding with one of the stages from the amount:

(wake, stage 2, stage 3, stage 4, MT).

Rule 2: Time-related conversion instructions apply to the following sequences, i.e., the conversion is carried out according to rem,rem,rem←rem,wake,rem,
rem,rem,rem←rem,stage1,rem,
rem,rem,rem←rem,stage2,rem,
rem,rem,rem←rem,uniden,rem,
←30 seconds applies to the duration of the epoch embedded in rem.

Rule 3: If the network proposes stage rem only over a time interval of maximally 90 seconds, the transformation is carried out according to rule stage1←rem.

Rule 4: Stage 1 allocations are converted into stage 2 allocations if the conditions of the following rules apply:

stage2,stage2,stage2←stage2,stage1,stage2,
stage3,stage2,stage3←stage3,stage1,stage3,
stage4,stage2,stage4←stage4,stage1,stage4,
and the stage] epochs do not last longer than one minute.

Rule 5: If stage1 epochs do not last longer than two minutes, the following rules are applied:

stage2,stage2,rem←stage2,stage1,rem,
rem,stage2,stage2←rem,stage1,stage2.

Said rules as defined by the invention are processed in the listed sequence.

The solution as defined by the invention is explained in greater detail in the following with the help of an exemplified embodiment in association with 8 figures of the drawings, in which:

FIG. 2 is a block diagram of the arrangement as defined by the invention.

FIG. 3 is a process flow diagram of the important program blocks for generating a sleep profile.

FIG. 1 shows that the active electrode is arranged in the region of the forehead of the test person in the form of an electrode strip 1.

Due to the design as defined by the invention, said electrode strip 1 can be easily secured on the skull without the help of another person. It permits freedom of movement while sleeping to the greatest possible extent and it is not perceived as annoying because of the design and arrangement as defined by the invention.

Figure 1:
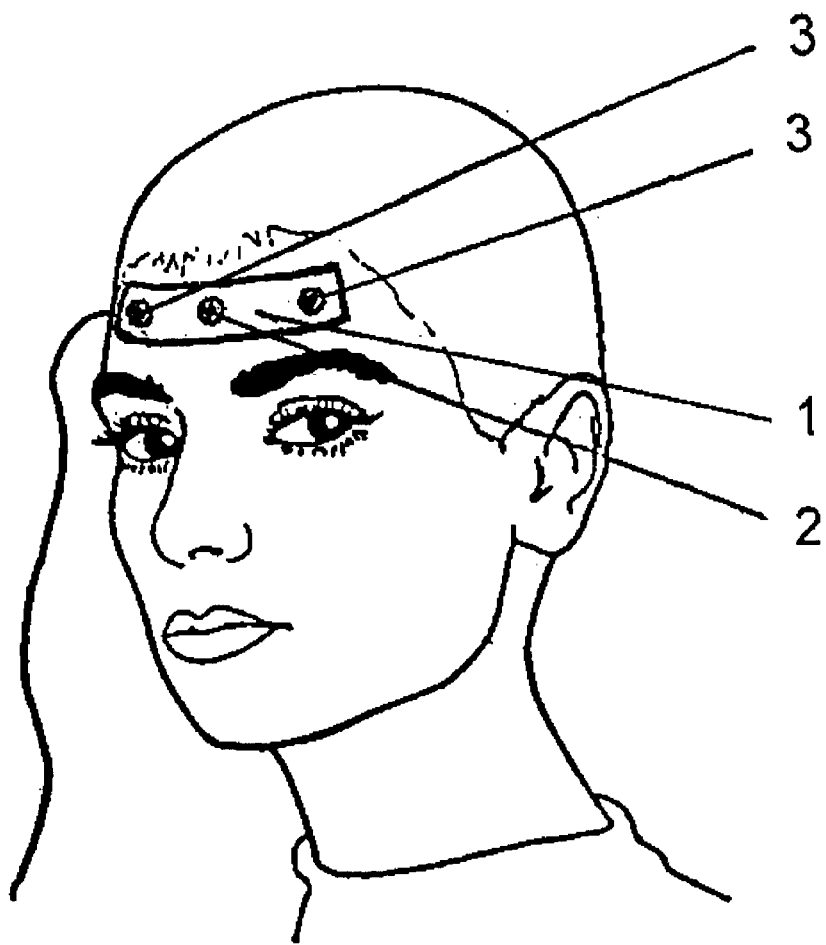
FIG. 1 shows the arrangement of the active electrode (electrode strip with preamplifier) in the region of the forehead of the test person.

In order to keep interference stray pick-up as low as possible, the principle of the difference amplifier was employed as shown in FIG. 1. This requires three electrodes. While one electrode, namely the center electrode establishes the reference point as ground and reference electrode 2, the difference of the other two electrodes 3 is amplified by the circuit with factor 100. The high-pass filter ($f_g$=0.03 Hz) connected upstream of each of said two other electrodes eliminates the dc voltage component of the two signals, which is not important for the evaluations.

The forehead position above the nose as close as possible to the hairline serves as orientation for mounting the ground and reference electrode 2 as well as the preamplifier part connected to the latter, whereby the electrodes 3 for bipolar lead-off are mounted in a horizontal line to the right and left of ground and reference electrode 2 with a fixed spacing of about 3.5 cm between each other.

Self-adhesive EKG-electrodes were found to be particularly suitable for long-term pick-up while sleeping. The gel does not dry out even after 10 hours and the electrodes excellently adhere to the forehead during the entire time.

The aforementioned EEG-signals are supplied to the battery-operated hand-held device 4, for example via a cable, said device being the measured-value receiving, storing and analysis unit. From the active electrode, which is located in electrode strip 1 on the forehead of the test person, the EEG-signal is transmitted to the battery-operated hand-held unit 4 with filter 5, amplifier 6, A/D converter 7, microcontroller 8 and memory 9, said unit being equipped, furthermore, with a keyboard and a display, via an interface, unit 4 can be connected to a computer, for example a personal computer 10 preferably via a glass fiber cable.

Now, FIG. 3 shows the process flow diagram with the important program blocks for generating a sleep profile. The characteristics or raw EEG-data, which already have been extracted, are transmitted from the hand-held unit to the PC as EEG load 11. In the transmission of raw data, characteristic extraction 12 has to take place on the PC-side. Subsequently, a classification 13 of each individual epoch of the night of sleep takes place by means of the instructed neural networks. The resulting sleep profile is subjected to a context analysis by a rule-oriented algorithm and corrected accordingly in the form of a smoothing of stage allocations 14. The last step is the transformation of the computed course of the sleep into a graphical representation of the actual sleep profile 15.

Figure 4:
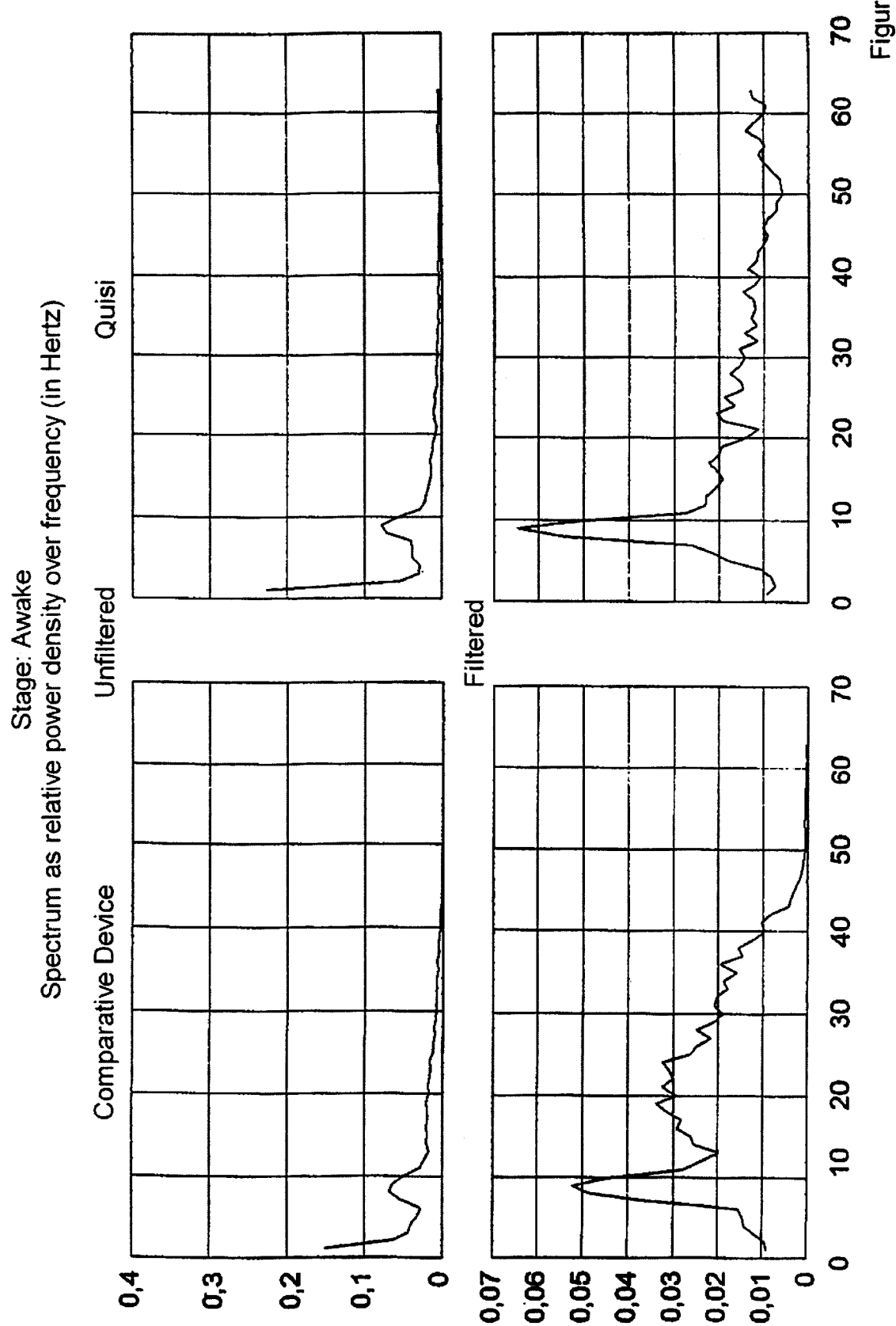
FIG. 4 shows a comparison of the unfiltered and filtered power spectra of a standard device with those of the solution as defined by the invention.

Now, in FIG. 4, the unfiltered and the filtered power spectra of a standard unit are compared with those of the solution as defined by the invention for the "wake" stage. The standard device is a "Nihen Koden Neurofax 21". The device as defined by the invention is called "QUIST". The spectra recorded with the two devices clearly show the alphapeak at 8–10 Hz, which is typical for the relaxed wake state.

Figure 5:
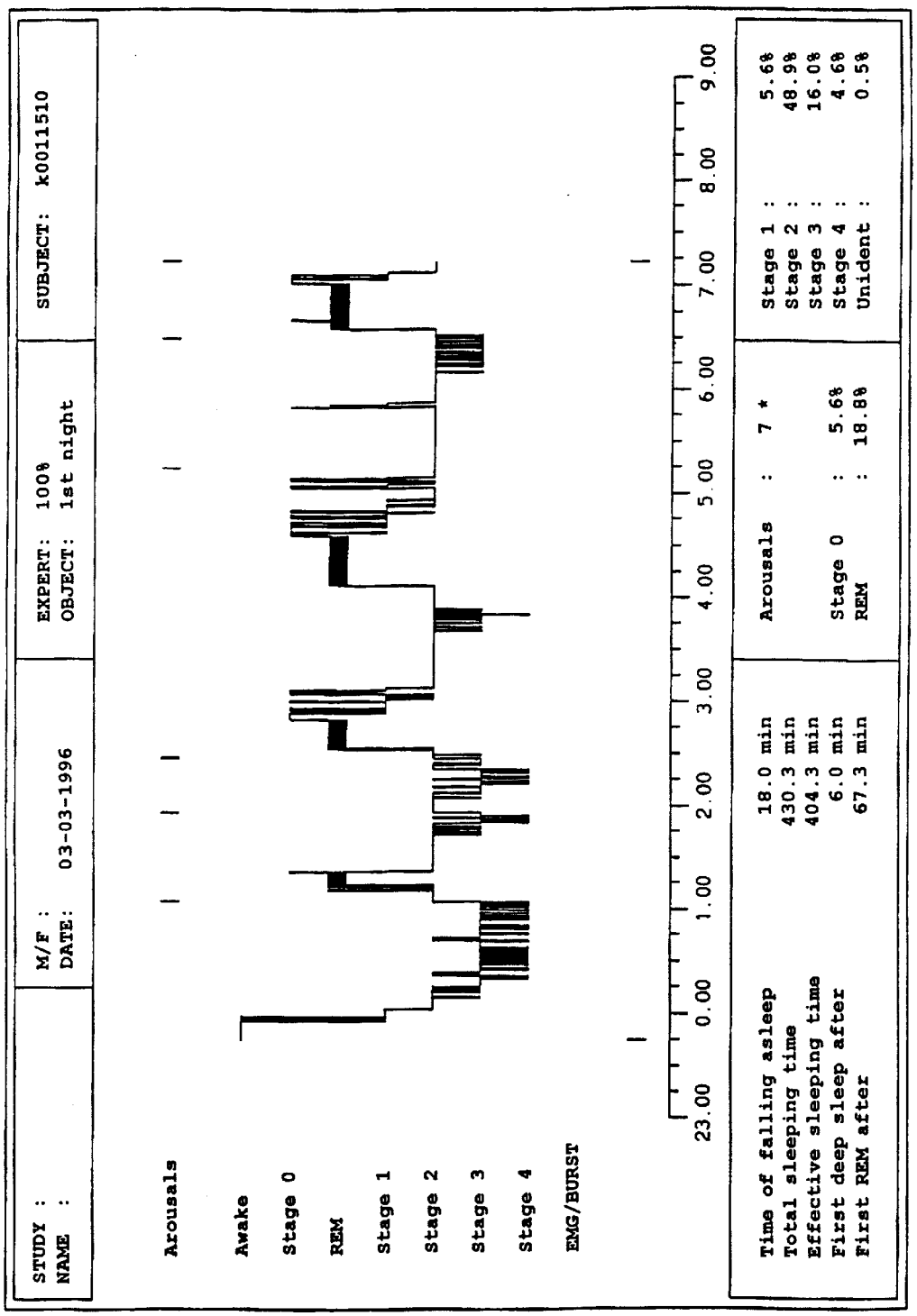
FIG. 5 shows the sleep profile of test person K 11510 generated by an expert or sleep stage scorer.
Figure 6:
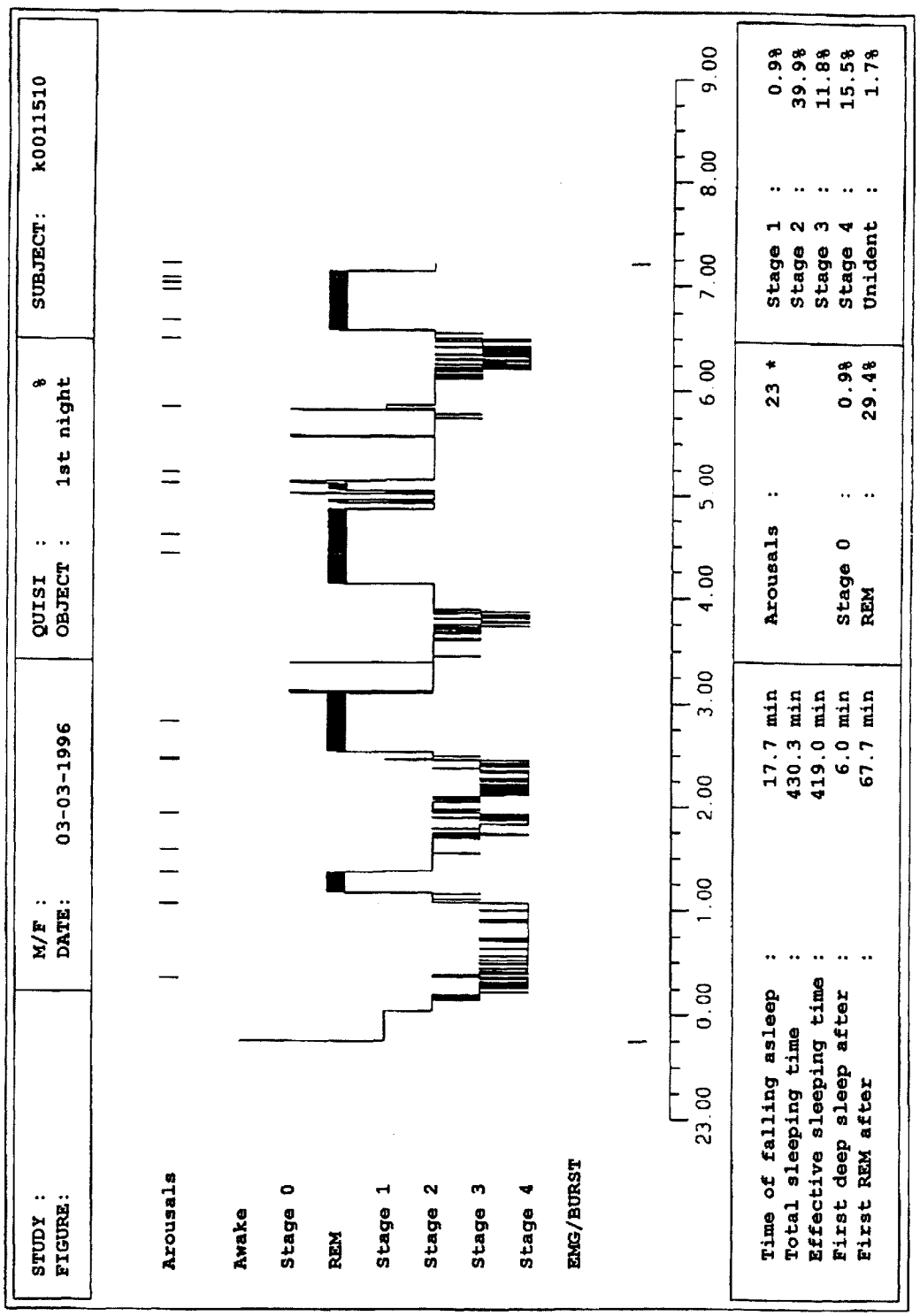
FIG. 6 shows the sleep profile of test person K 11510 generated with the help of the solution as defined by the invention.
Figure 7:
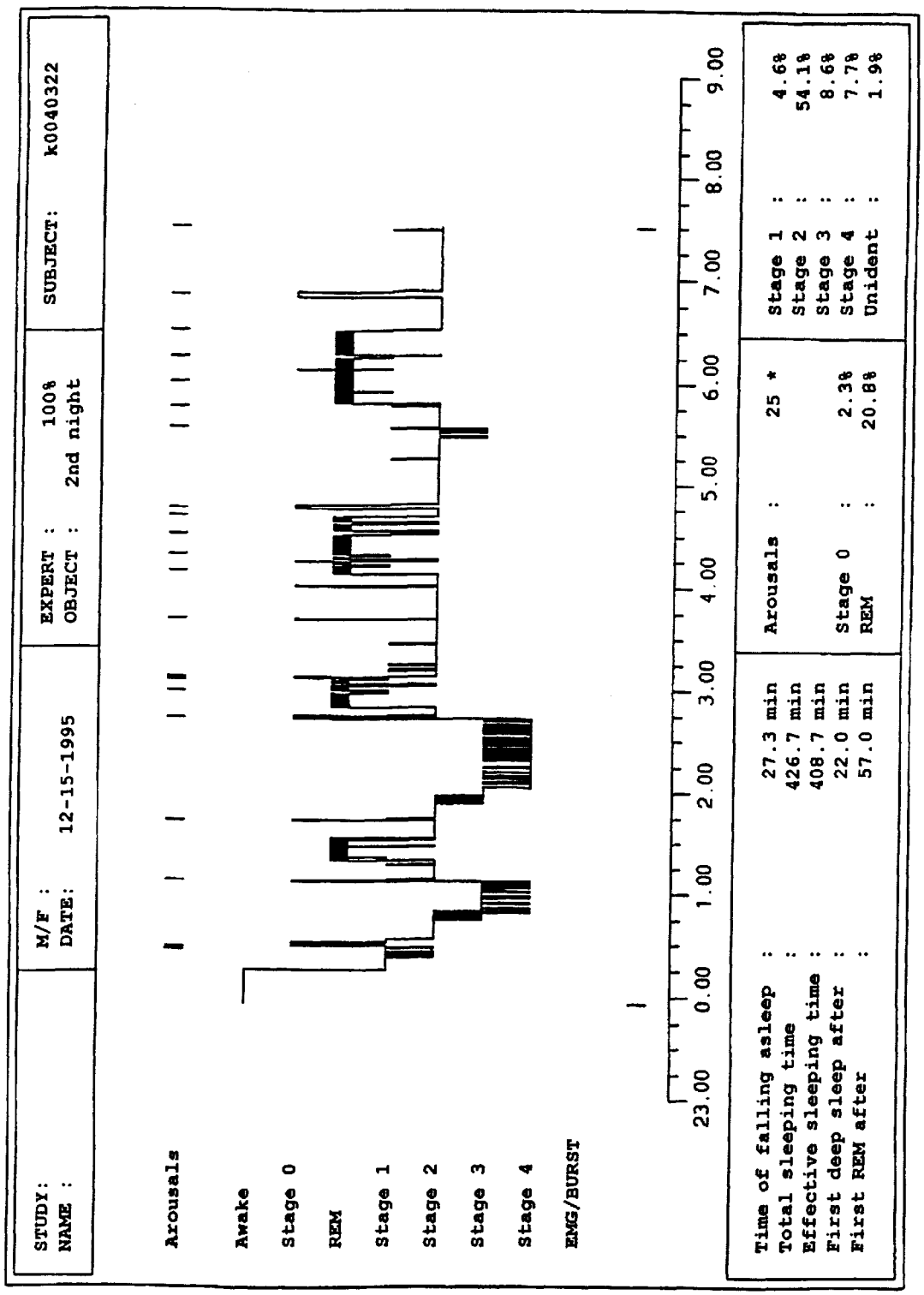
FIG. 7 shows the sleep profile of test person K 40322 generated by an expert or sleep stage scorer.
Figure 8:
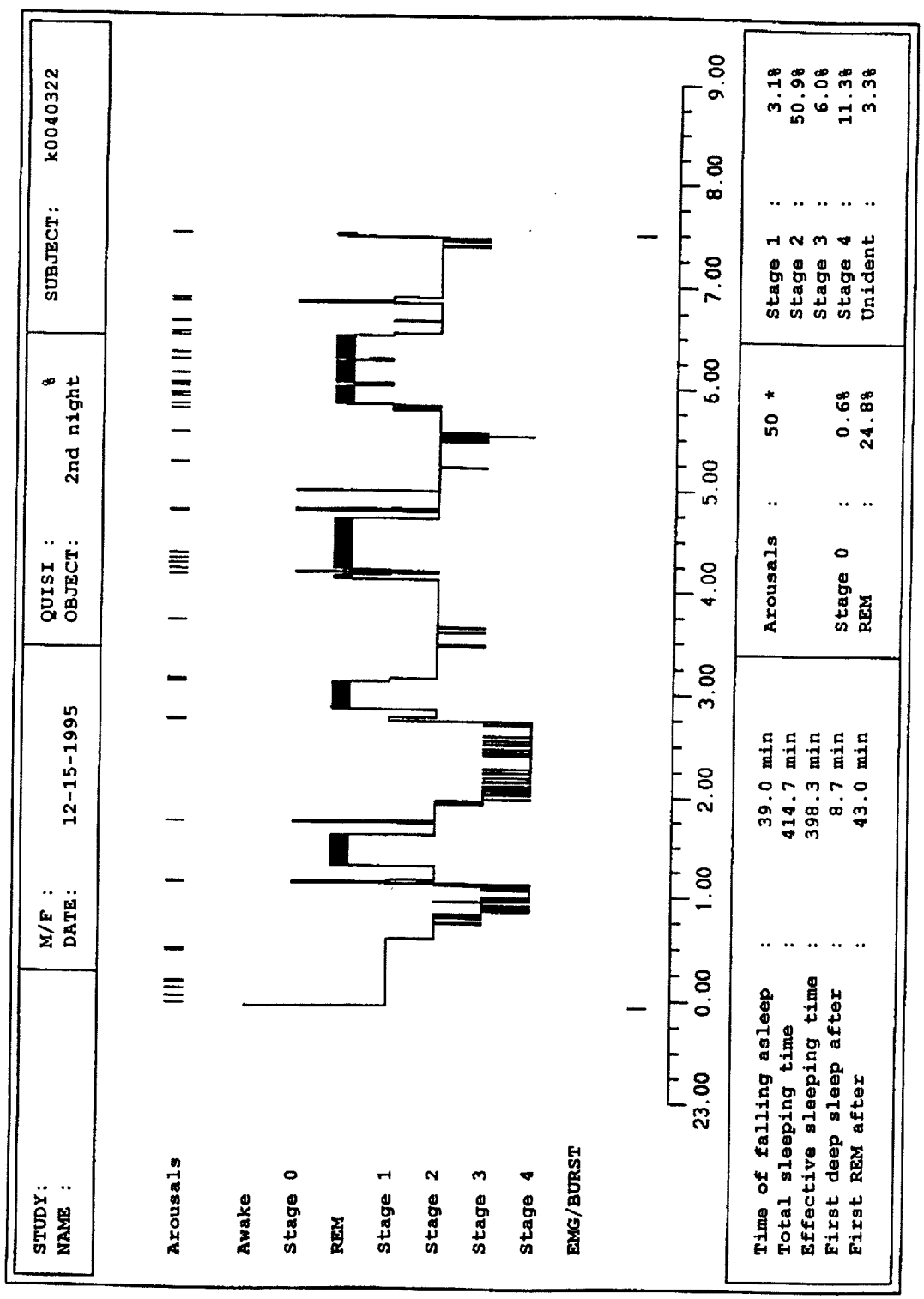
FIG. 8 shows the sleep profile of test person K 40322 generated with the help of the solution as defined by the invention.

FIGS. 5 to 8 show the sleep profiles to be compared. Said sleep profiles were generated in two selected nights by an expert, on the one hand, and by means of the QUISI solution as defined by the invention. FIGS. 5 and 7 show the profiles generated by the expert. The profiles automatically generated by the solution ("QUISI") as defined by the invention are shown in FIGS. 6 and 8. The profiles compared in each case show very good conformity both with respect to their curves and in terms of percentage distribution.

It was possible in the past few weeks to demonstrate such very good conformity again in a comparison of the profiles generated with the solution as defined by the invention with the profiles generated by experts within the framework of comparative tests carried out on over 60 sick test persons.

Therefore, it was possible for the first time by means of the solution as defined by the invention to develop a device and a method for the determination of sleep profiles which automatically generate a sleep stage classification with a grading of about 85% (crosscorrelation) with negligible discomfort to the sleeper caused by additional technical equipment in the ordinary environment of the sleeper, permitting in this way very good ambulatory diagnoses, whereby said newly developed arrangement, furthermore, is characterized by minimal manufacturing expenditure as well as practical equipment technology with high operational safety and reliability, which can be handled by each patient on his or her own in a simple manner and which, furthermore, is capable of registering even a 24-hour continuum in a simple and physiologically objective manner at favorable cost.

What is claimed is:

1. A method of determining sleep profiles, comprising the steps of:
    filtering an analog signal electroencephalographically detected and tapped off on a patient in the region of the forehead symmetrically to the nose root by using three sensors;
    amplifying and digitizing said signal for further processing, and subsequently compressed according to characteristics;
    storing and transmitting said signal to a computer for classifying said signal according to sleep stages by use of populations of neural networks topologically optimized by genetic and evolutionary algorithms;
    visualizing said signals and profiles, to enable interactive processing.

2. The method of determining sleep profiles according to claim 1, wherein for the step of digitizing a sample rate of 128 values per second has been chosen at a resolution minimum of at least 10 bits.

3. The method of determining sleep profiles according to claim 1, wherein the method comprises Fourier transformation of the EEG-signal analogously amplified and filtered and the method further comprising the step of extracting the following characteristics:
    Accumulated power density in the range of 1 to 4 Hz based on the overall power density (characteristic m1);
    Accumulated power density in the range of 5 to 7 Hz based on the overall power density (characteristic m2);
    Accumulated power density in the range of 8 to 11 Hz based on the overall power density (characteristic m3);
    Accumulated power density in the range of 12 to 14 Hz based on the overall power density (characteristic M4);
    Accumulated power density in the range of 15 to 30 Hz based on the overall power density (characteristic m5);
    Accumulated power density in the range of 31 to 63 Hz based on the overall power density (characteristic m6);
    Frequency at 25% of the overall power density (characteristic m7);
    Frequency at 50% of the overall power density (characteristic m8);
    Frequency at 75% of the overall power density (characteristic m9);
    Frequency of the maximal power density value in the range of 1 to 4 Hz (characteristic m10);
    Frequency of the maximal power density value in the range of 8 to 14 Hz (characteristic m11);
    Frequency of the maximal power density value in the range of 21 to 30 Hz (characteristic m12);
    Accumulated power density in the range of 50 to 60 Hz based on the overall power density (characteristic m13); and
    Number of the epoch based on the total number of epochs (characteristic m14), which consists of populations of 8 to 30 instructed neural networks and rules including the context of the epochs in the classification.

4. The method of determining sleep profiles according to claim 3, wherein for enhancing generalization capabilities of the networks, a standardization is carried out, whereby the range of each characteristic is transformed to be represented by the range between −2.0 and +2.0 and offered to the network as input data.

5. The method of determining sleep profiles according to claim 3, wherein instructed networks perform the stage allocations to each epoch.

6. The method of determining sleep profiles according to claim 1, wherein three populations of n=8 networks each are simultaneously employed, whereby one network in each case was instructed with the data of one night.

7. The method of determining sleep profiles according to claim 6, wherein said classification is first carried out separately with each network population, whereby the network populations differ from each other in that they were instructed on the basis of 12 (characteristics m1 to m12), 13 (characteristics m1 to m13) and 14 characteristics respectively, so that the networks of population 1 have 12 input units, the networks of population 2 have 13 input units and the networks of population 3 have 14 input units, wherein the number of output units remains fixed at 7 for all networks in accordance with the number of classes.

8. The method of determining sleep profiles according to claim 1, wherein an output unit with maximal excitation is determined for each network.

9. The method of determining sleep profiles according to claim 1, wherein reproduction of the sleep stages takes place in 7 natural numbers and that the median over all network-specific decisions supplies the respective classes to which the respective epoch is classified.

10. The method for determining sleep profiles according to claim 9, wherein a robust classifier is produced from synergy effects of three populations of said neural networks in that the median of the three population decisions is formed.

11. The method for determining sleep profiles according to claim 1, wherein context rules are employed, such context rules enhancing the sleep profiles via smoothing algorithms.

12. An arrangement for determining sleep profiles said arrangement adapted to be placed on a patient's forehead, comprising:

an electrode strip (1) having a pre-amplifier placed on the forehead of the patient, said electrode strip operating based on one single frontal EEG-channel;

an autonomously operating microprocessor-controlled measuring and analysis unit connected to said electrode strip and supplied with energy via a battery, said measuring and analysis unit comprising:

a filter bank;

a final amplifier;, an A/D-converter;

a microcontroller with internal system software memory; and an operating keyboard and display; and a potential-free serial PC-interface arranged on said measuring and analysis unit, via which interface said measuring and analysis unit is connected to a commercially available PC with special software for adaptive classification by populations of neural networks for visualizing the electric potentials of the brain as well as sleep and wake profiles.

13. The arrangement for determining sleep profiles according to claim 12, wherein when said electrode strip (1) with said preamplifier is arranged on the forehead symmetrically with the root of the nose, solely said information tapped off as potential difference in the region of the forehead of the patient is processed further for determining sleep and wake profiles.

14. The arrangement for determining sleep profiles according to claim 12, further comprising a separate unit for storing original electric potentials of the brain is connected to said electrode strip (1) in an on-line mode.

15. The arrangement for determining sleep profiles according to claim 12, wherein said preamplifier is arranged on the center electrode of the electrode strip, so that the EEG-signal as an analog signal is already subjected near its lead site to amplification and the signal source is so subjected mainly to an impedance conversion.

16. The arrangement for determining sleep profiles according to claim 12, wherein said filter bank consists of a 50-Hz filter, a low-pass filter and a high-pass filter, said filter switched together supplying a bandpass filter with $f_u$=0.5 Hz and $f_o$=64 Hz.

17. The arrangement for determining sleep profiles according to claim 12, further comprising at least a 10-bit A/D-converter employed in association with an 8-bit microcontroller for further processing the signal.

* * * * *

UNITED STATES PATENT AND TRADEMARK OFFICE
CERTIFICATE OF CORRECTION

BPATENT NO. : 6,272,378 B1
DATED : August 7, 2001
INVENTOR(S) : Baumgart-Schmitt It is certified that error appears in the above-identified patent and that said Letters Patent is hereby corrected as shown below:

<u>Title page,</u>
Item [22], the PCT filing date should read:
-- November 17, 1997 --

Signed and Sealed this

Twentieth Day of August, 2002

*Attest:*

*Attesting Officer*

JAMES E. ROGAN
*Director of the United States Patent and Trademark Office*